(12) United States Patent
Beck (10) Patent No.: US 11,241,328 B2
(45) Date of Patent: Feb. 8, 2022

(54) COUPLEABLE SUPPORT SPLINT

(71) Applicant: BAUERFEIND AG, Zeulenroda-Triebes (DE)

(72) Inventor: André Beck, Apfelstädt (DE)

(73) Assignee: BAUERFEIND AG, Zeulenroda-Triebes (DE)

( * ) Notice: Subject to any disclaimer, the term of this patent is extended or adjusted under 35 U.S.C. 154(b) by 485 days.

(21) Appl. No.: 15/126,090

(22) PCT Filed: Feb. 12, 2015

(86) PCT No.: PCT/EP2015/052949
§ 371 (c)(1),
(2) Date: Sep. 14, 2016

(87) PCT Pub. No.: WO2015/139891
PCT Pub. Date: Sep. 24, 2015

(65) Prior Publication Data
US 2017/0119570 A1    May 4, 2017

(30) Foreign Application Priority Data
Mar. 20, 2014  (DE) .......................... 102014004261.8

(51) Int. Cl.
*A61F 5/058*  (2006.01)
*A61F 5/10*  (2006.01)

(52) U.S. Cl.
CPC ...... *A61F 5/05875* (2013.01); *A61F 5/05825* (2013.01); *A61F 5/10* (2013.01)

(58) Field of Classification Search
CPC .. A61F 5/05875; A61F 5/0118; A61F 13/105; A61F 5/10; A61F 5/05866; A61F 5/50; A61F 5/05825; A61B 19/04; A41D 19/01588
See application file for complete search history.

(56) References Cited

U.S. PATENT DOCUMENTS 1,220,476 A * 3/1917 Ujdur .................. A61F 5/05875
602/22
1,837,691 A   12/1931 Thigpen
2,095,603 A   10/1937 Langdon
(Continued)

FOREIGN PATENT DOCUMENTS

DE      1124633     3/1962

OTHER PUBLICATIONS

International Preliminary Report on Patentability and Written Opinion of the International Searching Authority regarding International Application No. PCT/EP2015/052949, dated Sep. 20, 2016. Translation provided by Gleiss & Grosse.
(Continued)

*Primary Examiner* — Ophelia A Hawthorne
(74) *Attorney, Agent, or Firm* — Harness, Dickey & Pierce, P.L.C.; Stephen T. Olson (57) ABSTRACT

An articular support for supporting bones connected to one another by joints, includes at least one support splint, which is structured in at least two segments. The support splint has at least one guide per segment to receive a reinforcing element for longitudinal coupling of the at least two segments and coupling means for transverse coupling of this support splint to at least one additional neighboring support splint.

16 Claims, 7 Drawing Sheets

(56) References Cited

U.S. PATENT DOCUMENTS

| | | | | |
|---|---|---|---|---|
| 2,573,715 | A | | 11/1951 | Kelly |
| 3,913,570 | A | | 10/1975 | Madden et al. |
| 4,243,026 | A | | 1/1981 | Barber |
| 4,441,489 | A | * | 4/1984 | Evans ................ A61F 5/10 602/22 |
| 4,719,906 | A | * | 1/1988 | DeProspero ............ A61F 5/013 602/21 |
| 4,765,320 | A | * | 8/1988 | Lindemann ........... A61F 5/0118 602/22 |
| 5,328,448 | A | * | 7/1994 | Gray, Sr. ................ A61F 5/013 482/44 |
| 5,848,983 | A | * | 12/1998 | Basaj .................. A61F 5/05866 602/22 |
| 2003/0078531 | A1 | * | 4/2003 | Nguyen ............. A61F 5/05866 602/22 |
| 2003/0097084 | A1 | | 5/2003 | Bonutti |
| 2005/0027223 | A1 | * | 2/2005 | Nguyen ............. A61F 5/05875 602/23 |
| 2005/0251078 | A1 | * | 11/2005 | Fleischmann ........ A41D 13/087 602/22 |
| 2006/0211964 | A1 | | 9/2006 | Farrell et al. |
| 2008/0039767 | A1 | * | 2/2008 | Nordt, III ............ A41D 13/088 602/64 |

OTHER PUBLICATIONS

International Search Report (German and English) for PCT/EP2015/052949, ISA/EP, Rijswijk, NL, dated May 6, 2015.
Written Opinion of the ISA, (German) ISA/EP, Rijswijk, NL, dated May 6, 2015.
Office Action received for the Indian Patent Application No. 201627030695, dated Dec. 15, 2020, 2 pages.

* cited by examiner

COUPLEABLE SUPPORT SPLINT

CROSS-REFERENCE TO RELATED APPLICATIONS

This application is a 371 U.S. National Stage of International Application No. PCT/EP2015/052949, filed Feb. 12, 2015, which claims the benefit of and priority to German Patent Application No. 10 2014 004 261.8, filed Mar. 20, 2014. The entire disclosures of the above applications are incorporated herein by reference.

FIELD

The invention relates to medical aids, in particular orthotic devices for supporting body parts, in particular an articular support for the support or fixation of articulated bones, such as the fingers or spine. The articular support comprises at least one support splint, which is divided into segments that can be applied to the bones, which are connected in an articulated manner. According to the invention, this segmented support splint can be reinforced in the longitudinal direction by means of reinforcing elements and can be coupled by means of transverse coupling elements to similar neighboring support splints.

BACKGROUND

Bones of the body that are connected in an articulated manner, for example, the fingers and thumbs of the hand as well as the toes but also portions of the spine, in particular the cervical spine and the lumbar spine, must be supported, i.e., supported in their mechanical function and mobility, or immobilized, i.e., secured, permanently or temporarily for medical reasons after a trauma or wear. Fixation of the articular connection is necessary in particular in the event of fractures, capsule tears or tendon injuries as well as in inflammatory processes and similar joint conditions. To do so, the natural mobility, in particular the joint mobility of the bones relative to one another, should be suppressed either temporarily or completely. Bandages or orthotic devices are medical aids, which are applied to the articulated bones, for example, the fingers especially in the form of support plates, support splints and/or pads. In a simple form, these are usually devices formed by cold formable, i.e., malleable, metal splints, which are held on the joint by means of bandages or flexible or elastic textile bodies. One disadvantage here is that a medically required stepwise reduction in mobility of a joint that is initially completely secured with these traditional support orthotic devices, for example, cannot be guaranteed because either a complete immobilization of the joint or mere mechanical support of mobility are available as alternatives. In particular, known orthotic devices of this generic type cannot be adapted sufficiently well to the respective individual degree of support or fixation of the joint that is required, in particular in support of body parts with multiple joints, such as fingers or the various components of the spine.

In addition, in particular in the area of hand orthotic devices, there is often a medical necessity to mechanically support or secure only individual finger joints of the hand or multiple finger joints, depending on the pathological condition. For example, it might be necessary to immobilize the base joint of a finger but to support the end joint of the finger only mechanically while it remains fundamentally mobile. Furthermore, it may be necessary for a single injured finger to be supported mechanically by means of the neighboring healthy fingers in a finger bandage, wherein the injured finger is completely immobilized in an acute stage of injury, but at a later point in time the injured finger joint is to be exercised to an increasing extent by means of the neighboring mobile healthy fingers.

SUMMARY

The invention has taken as its object to provide an orthotic device, in particular a hand and finger orthotic device, which can solve the aforementioned problems.

The invention is providing for this purpose a modular system, especially for use as or in a hand and finger orthotic device, which can be adapted to the respective given factors of the injury and the required measures through simple intervention on the part of the treating physician, the patient and in particular the orthopedic technician so that the aforementioned requirements are met.

The subject matter of the present invention is an articular support for supporting bones connected to one another by joints, using at least one support splint, which is structured in at least two segments, each segment being assignable to a bone and the support splints having per segment at least one guide for receiving a reinforcing element for longitudinal coupling of the at least two segments and coupling means for transverse coupling of these support splints to at least one additional support splint adjacent thereto.

There are preferably at least two similar support splints that can be coupled transversely to one another.

At least one detent is preferably formed on at least one segment of the one support splint for meshing with a groove on a segment of the neighboring support splint.

Alternatively, a guide on at least one segment of the one support splint for receiving a transverse coupling element is preferable as a coupling means for engagement in a guide on a segment of the neighboring support splint.

This guide is in particular designed as at least one strap on the support splint. Alternatively, the guide is designed as a channel inside the support splint.

The segments are preferably separated from one another by notching and/or areas of thinner material on the splint.

The subject matter of the invention is also a hand orthotic device comprising the articular support according to the invention described herein, wherein the bones are finger bones.

DETAILED DESCRIPTION OF THE INVENTION

The subject matter of the present invention is primarily an articular support in support of bones that are joined to one another by joints and have at least one segmented support splint. According to the invention, this support splint is structured in at least two segments, wherein in particular each segment can be assigned to one, in particular exactly one bone, to be supported.

The segments are designed in particular to be flexible or articulated relative to one another due to areas of thinner material or notching of the support splint base material in order to follow, in a flexible or articulated manner, the natural course of the joint of the articulated bones that can be assigned to one another. Thus, a function of the support splint that supports the joint movement can be achieved in particular.

However, the invention also provides that the support splint has at least one guide to receive a reinforcing element, in particular per segment. According to the invention a reinforcing element that can be inserted into the guide of the mechanical joint coupling of these at least two segments, in particular neighboring segments of this support splint serves this purpose. In one variant more than two, in particular all segments present on the support splint are or can be coupled by means of at least one reinforcing element.

The guides provided according to the invention on the segments serve in particular to receive a reinforcing element, which bridges at least one of the segment boundaries in order to reduce or completely suppress the mobility of the support splint at this segment boundary. Typically, a material strip manufactured from a rigid inelastic material can be inserted as a reinforcing element. A cold formable material strip is preferably used as the reinforcing element. Alternatively, a cold strip, in particular a thermoformable cold strip may be used. Due to the deformability of the reinforcing element, the two segments connected to the support split may also be secured in a certain predetermined angular position. Reinforcing elements made of metal and thermoformable plastic are known per se in the field of orthopedics.

Depending on the medical indication or course of treatment, for example, a reinforcing element, which was first inserted into the support splint to block the mobility of the bones connected in an articulated manner can be simply removed at a later point in time to allow a movement of the known elements connected in an articulated manner.

The at least one guide is designed in particular to receive a reinforcing element for longitudinal coupling of the at least two segments as a strap, placed on the base body of the support splint. In an alternative or additional embodiment, at least one channel is formed in the base body of the support splint, the reinforcing element being accommodated and guided therein. In addition, a flexible catch may be provided at the tip of the support splint and/or in the area of the end of each segment of the support splint, blocking the inserted reinforcing element to prevent displacement and thus protecting it, in particular to prevent the reinforcing element from falling out.

In a special variant of this embodiment, it is provided that this spring catch is provided in a plurality of segments formed on the support splint, only the spring catch located at the end of the reinforcing element blocks the reinforcing element, depending on the length of the inserted reinforcing element, while the spring catches, which are within the extent of the reinforcing element, i.e., in particular on the bridging segment beneath the reinforcing element, are not engaged directly with the end of the reinforcing element due to this spring action but instead remain folded back in the base body of the support splint. This permits an individual shortenability of the reinforcing element, regardless of the total length and total number of the segments on this support splint, while, at the same time, the shortened reinforcing elements are blocked by means of the spring detents to prevent displacement.

The invention also provides that the support splint has means which enable a transverse coupling of this support splint with at least one additional neighboring support splint, in particular one having a similar design. Thus in particular in conjunction with a finger orthotic device, a mechanical coupling of the support splints and thus of the neighboring fingers to be supported can be enabled. It is preferably provided here that this orthotic device for supporting the fingers is designed to be essentially modular and comprised of similar support splints. According to the invention, the support splint thus has in particular per segment at least one coupling element, which serves the function of transverse mechanical coupling of this support splint with at least one additional support splint, which is a neighbor to the former, in particular directly. It is provided here in particular that this neighboring transverse coupling support splint has essentially the same design. In other words, it is true in particular that the neighboring additional support splints are structured in at least two segments and at least one promising fixation to receive a reinforcing element for longitudinal coupling of the at least two segments. In addition, the neighboring additional support rail in particular also has at least one corresponding coupling means, in particular one for each segment, which serves to provide mechanical cross-coupling with the neighboring support rail.

In a special embodiment, the transverse couplability of neighboring support splints with one another can be limited to certain segments of the support splint by the coupling means provided according to the invention. To do so, it is provided in particular that the coupling means are designed selectively per segment and can be suppressed selectively per segment by a simple intervention measure. This takes place in the case when the coupling means are designed as detents, especially by targeted break-off of the detent on the segment for the case when the coupling means are designed as a transverse coupling element, by removal of the transverse coupling element on the segment.

In a preferred embodiment, the coupling means are designed on the support splint as at least one detent on at least one segment of the one support splint, which is designed for meshing with a groove on a segment of the neighboring support splint. Those skilled in the art are familiar with alternative form-fitting and/or force-locking coupling means. In addition to detents which engage in grooves, pushbuttons, locking pins and pins and nails with a clamping fit as well as rivets, screws, bolts and the like are preferred.

In a special embodiment, at least one guide is designed as the coupling element on at least one segment of the one support splint, which serves to receive a separate transverse coupling element. The transverse coupling element is guided mechanically in the guide so that it engages in a corresponding guide on a segment of the neighboring support splint. Such a transverse coupling element is designed, for example, in the form of a rigid strip or wire made of metal or plastic. In this special embodiment, it is particularly possible to couple two or more splints situated side by side by means of a transverse coupling element in a targeted manner. The selection of the support splints to be coupled transversely can be determined by a simple choice of the length of the transverse coupling element to be used. The guides on the at least one segment are designed in particular to receive the transverse coupling element in the form of straps placed on the base body of the support splint.

In a special embodiment of the invention as a hand orthotic device, it is therefore provided in particular that one or especially several of the support splints according to the invention are designed and/or connected to the base body in a force-locking and/or form-fitting manner, in particular reversibly connected to a base body, which serves as a hand support in particular and which can be fastened to the forearm in particular. Depending on the medical indication, one or more of the support splints according to the invention may thus be formed or mounted on the base body in order to support one or more fingers of the hand and thereby support or secure one or more of the finger joints of a finger. The invention now offers the possibility of mechanically linking together several neighboring support splints via the transverse coupling means provided according to the invention in order to achieve an orthopedically beneficial and individually adapted supporting effect for the finger joints.

The notching or areas of thinner material at the segment boundary additionally or alternatively serve to enable shortening of the support splint for individual adjustment of the support function depending on the medical indication, by the user, the physician and in particular the orthopedic technician in a simple procedure. The areas of thinner material thus serve as an "intended breaking point" and/or as a predetermined tooling approach for a cutting tool. In this embodiment of the invention, depending on the medical indication, identically designed support splints may each be shortened individually to limit the supporting effect to individual joints in a targeted manner, in particular to individual finger joints of individual fingers. In the unshortened basic form, the support splint serves to support the middle joint of the finger and the base joint of the finger, and in the further shortened form it serves to support only the base joint of the finger. In addition, the base form of the finger splint, in which the dimensions are intended for a middle finger, can be reconstructed by simple shortening to a shortened variant, which fits the small finger by means of the segmentation in a given position. In this way, a finger orthotic device can be assembled individually from similar support splints, which not only improves handling, while enlarging the orthopedic spectrum of applications, but also reduces the cost of manufacturing the orthotic device in a manner that saves on resources.

Accordingly, the invention also relates to a hand orthotic device, which has articular support, especially at least one, in particular two transversely couplable support splints each of which is structured in reinforcible segments. The bones referenced are the finger bones.

Figure 1:
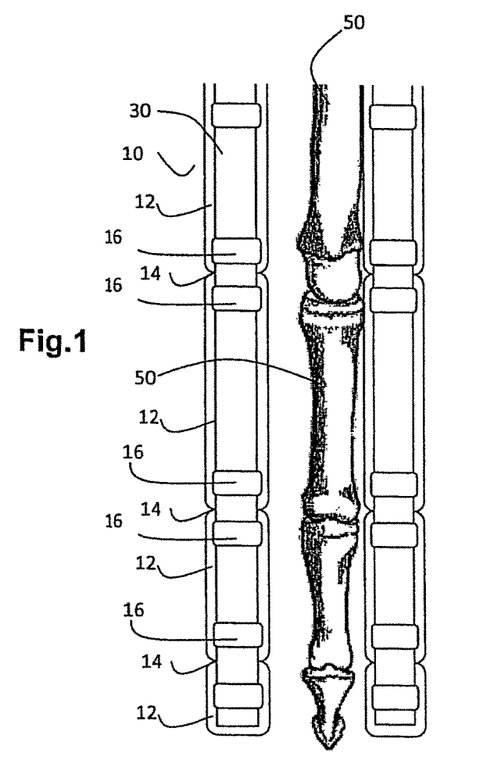
FIG. 1 shows a schematic design of the support splint of the articular support according to the invention.

FIG. 1A shows a schematic design of the support splint 10 of the articular support according to the invention, wherein the support splint is structured in segments 12. In addition, the support splint has notches or areas of thinner material 14, which serve to structure the support splint into at least two segments 12. The segments 12 can be adapted to the bones 50 in their articular connection to be supported, wherein a segment 12 can be assigned to a certain bone 50. In addition, the segments of the support splints have at least one guide 16, in which a reinforcing element 30, which can be reinforced mechanically by the notch of the flexible connection formed by the notch or the areas of thinner material 14. FIG. 1B shows as an example the assignment of each of the individual segments 12 to one bone 50 or each bone on the example of one finger of the hand.

Figure 2:
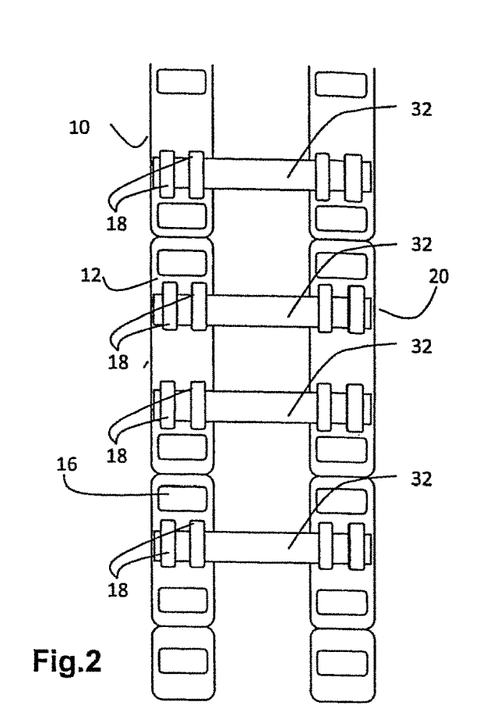
FIG. 2 shows two similarly designed support splints which are mechanically transversely coupled by coupling means in combination with transverse coupling elements.

FIG. 2 shows two similarly designed support splints which are mechanically transversely coupled by means of coupling means 18 in combination with 32. In the embodiment according to FIG. 2, the coupling means are designed as guides 18, wherein a transverse coupling element 32 is guided and comes into engagement with the corresponding guide 18 of the neighboring support splint 20. It is provided in particular that at least one separate coupling means is to be provided per segment for the transverse coupling, wherein the transverse coupling can be established selectively in segments. The segmentation of the support splint is thus preferably accomplished according to the invention by structural measures such as notching in the area of the segment boundaries and/or alternatively by areas of thinner material in the area of the segment boundaries. The at least two segments of a support splint are thus preferably separated from one another by notching and/or areas of thinner material on the splint. The notching and/or thinning of material preferably serves to enable mobility of the support splint in the manner of a film joint, so that the splint can follow the movement of the bones connected in an articulated manner, in order to support them mechanically.

Figure 3:
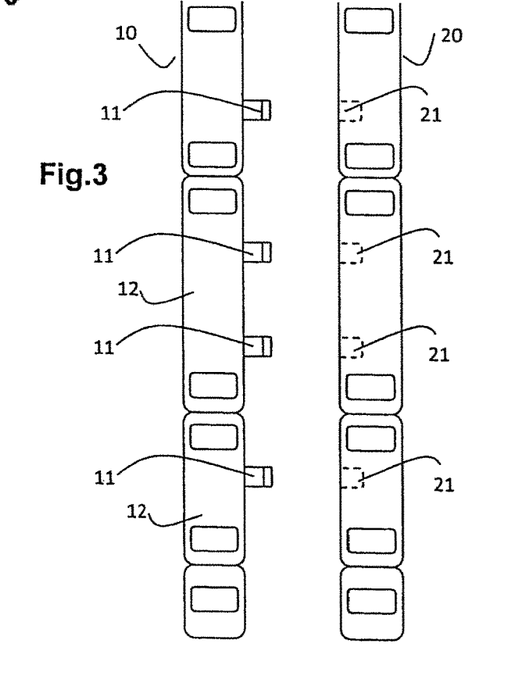
FIG. 3 shows an alternative embodiment of the coupling means for transverse mechanical coupling of neighboring support splints.

FIG. 3 shows an alternative embodiment of the coupling means for transverse mechanical coupling of neighboring support splints. Detents 11 are designed in segments on a support splint 10 and can engage with grooves 21 of a neighboring support splint 20 in order to bring about the transverse mechanical coupling.

It may be provided in particular that for the purpose of the simple modular design, support splint 10 and neighboring support splint 20 may have a similar design according to which base the support splint 10 and the support splint 20 each have detents 11 and grooves 21. For an overview, only the detents 11 are shown for the support splint 10, but only the grooves 21 for receiving the detents are shown for the support splint 20.

Figure 4:
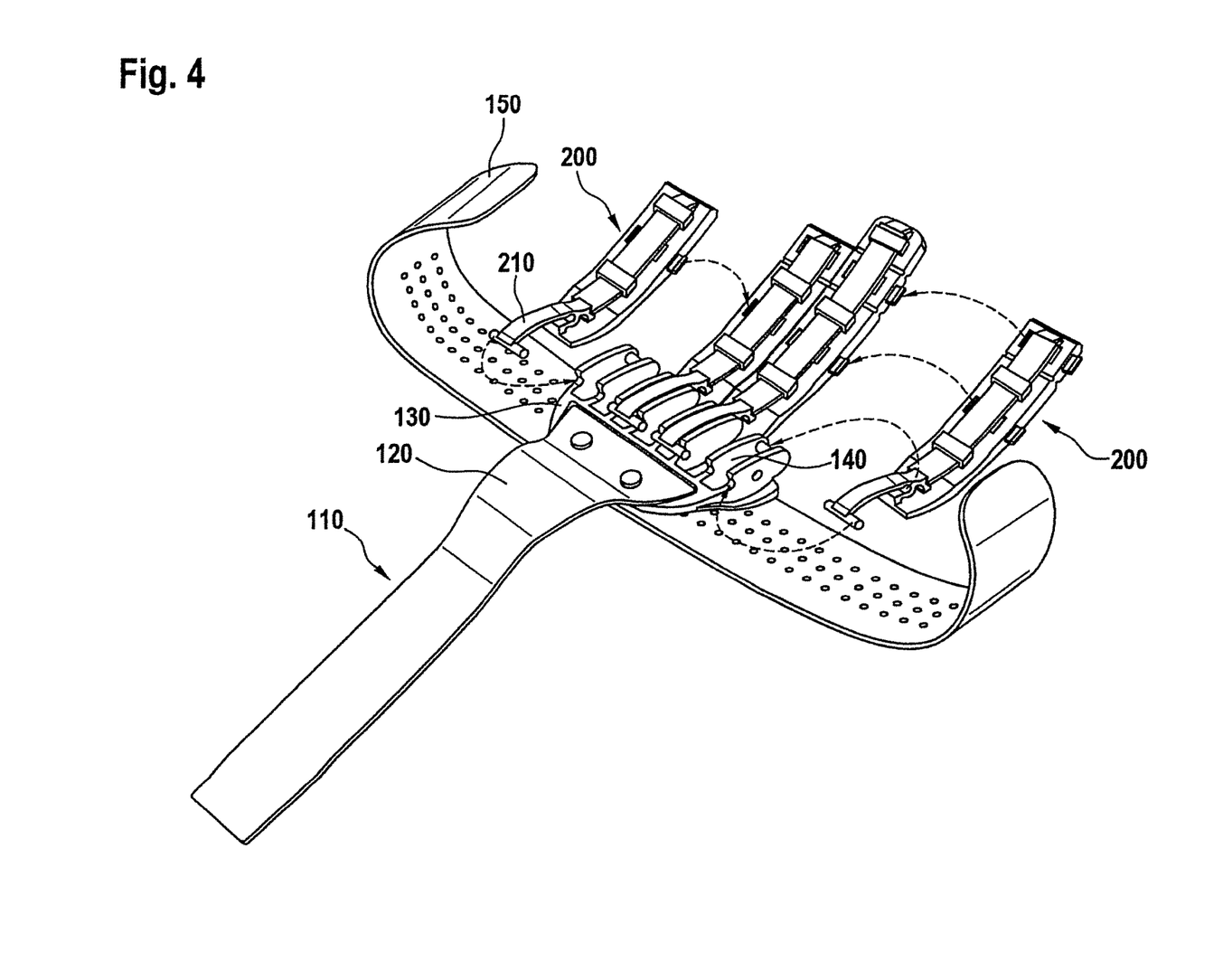
FIGS. 4-6, 7A, 7B and 8 show a further embodiment of the articular support according to the invention for use as a finger/hand orthotic device.

FIGS. 4 to 8 show a special embodiment of the articular support according to the invention for use as a finger/hand orthotic device. The invention is not limited to this application. Instead it illustrates the basic principle of the modular design of the articular support according to the invention. FIG. 4 shows a base body 110, which serves as a hand support, consisting of a receptacle 130 for receiving at least one support splint 200 via mechanical catch couplings 210 on the support splint 20, which can be engaged with counterparts 140 of the receptacle 130 of the base body 110. In addition, the base body 110 has a splint 120 and at least one belt 150 to reliably secure the base body. The design of the fixation of the base body, i.e., the hand support on the forearm here is diagrammed only schematically for the sake of simplicity. Those skilled in the art are familiar with suitable measures for secure fixation of a hand support on the forearm. As an alternative to the at least one girdle 150 shown here, the base body 110 can be inserted by means of the splint 120 into an essentially known middle hand/forearm orthotic device and affixed there.

Figure 5:
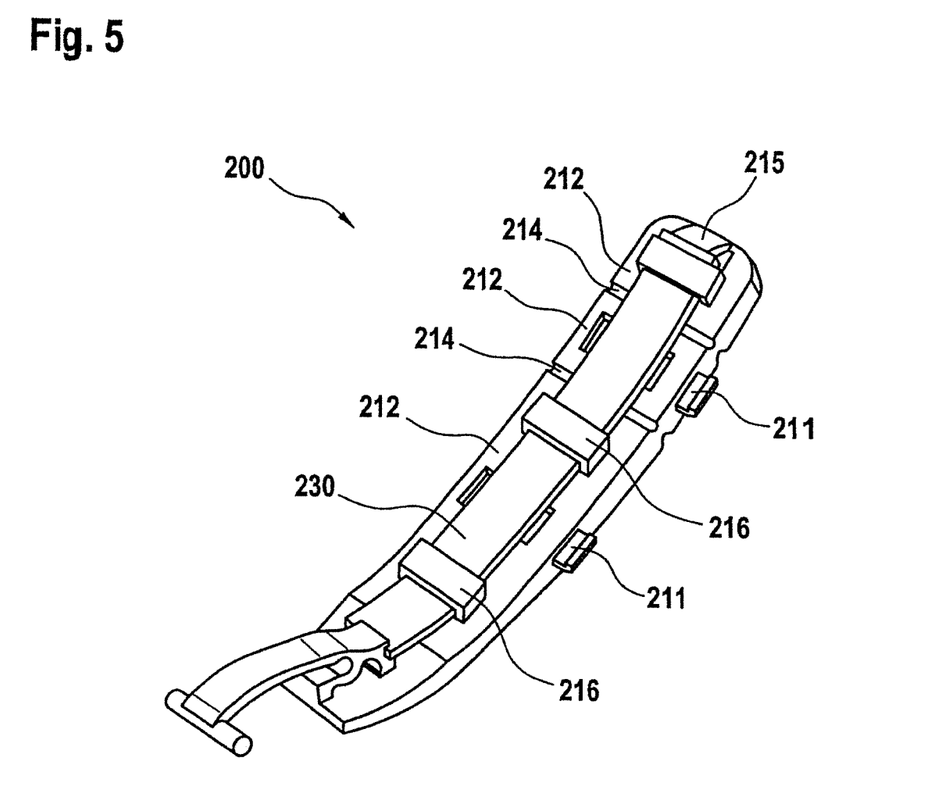

FIG. 5 shows a schematic diagram of one embodiment of the articular support according to the invention, such as that suitable for use on a finger/hand orthotic device, in particular for a modular design. The support splint 200 is divided into the segments 212 by areas of thin material 214. The dimensions of these segments are adapted to the size of the finger to be supported. Segments 212 have guides 216 on them in the form of bridges to receive a reinforcing element 230 in order to enable a mechanical reinforcement of the supporting splint 200 beyond the segment boundaries. To secure the reinforcing element 230, elastic catches 215 are provided at least on the end element in order to prevent the inserted reinforcing element 230 from slipping out of the support splint.

Figure 6:
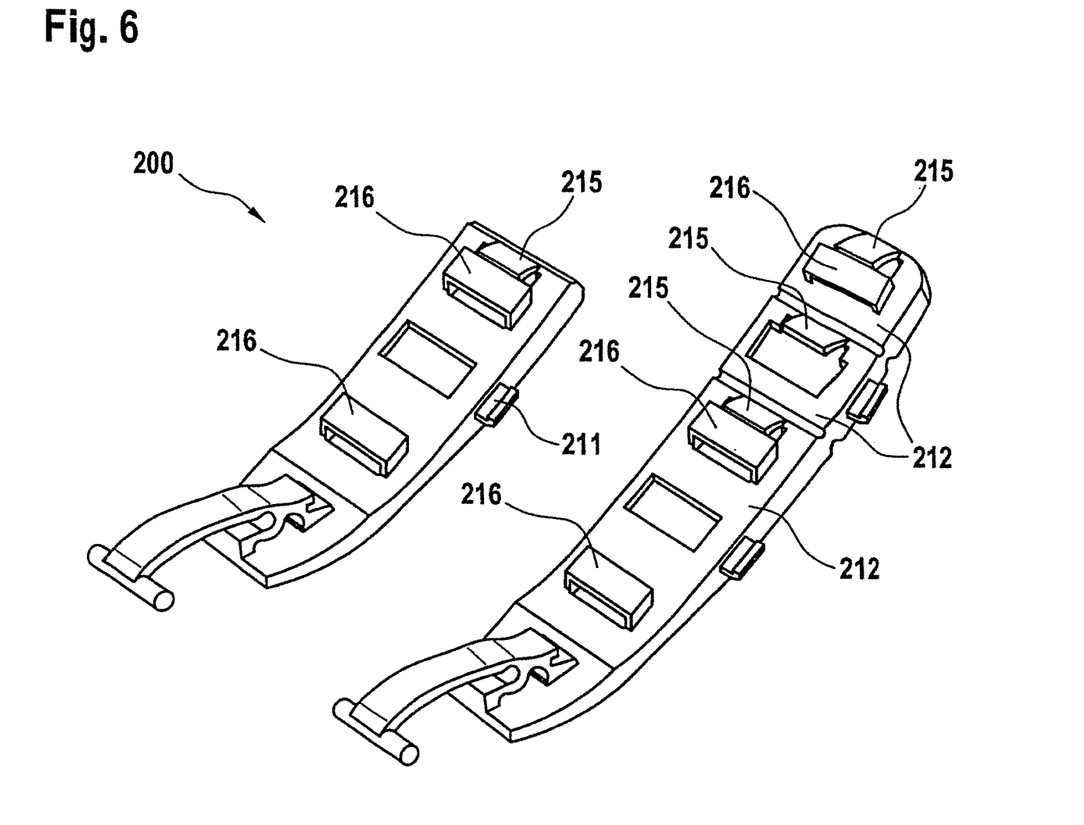

FIG. 6 shows the support splint 200 in its individual adaptability to the length to control its support function. Cuts can be made at the boundaries between the segments 212 through the areas of thinner material 214. To nevertheless permit a secure seating of a reinforcing element 230 on the support splint 200, elastic catches 215 which can become engaged with the reinforcing element 230 to be inserted are provided in each potential end segment 212. This figure shows in particular the modular aspect of the articular support according to the invention. Not only do neighboring support splints have a similar design, but also the special embodiments of the segments on a support splint, in particular in conjunction with the spring catches 215, permit individual adaptation and design of the finger/hand orthotic device, starting from a single support splint having a similar design. This can be mass produced in particular as an injection-molded part using a single mold.

In the embodiment according to FIG. 6, the support splints 200 have detents 211, which come into engagement in grooves (not shown in the figure), which are preferably formed opposite the same support splint in order to enable the transverse coupling of at least two support splints with one another.

Figure 7A:
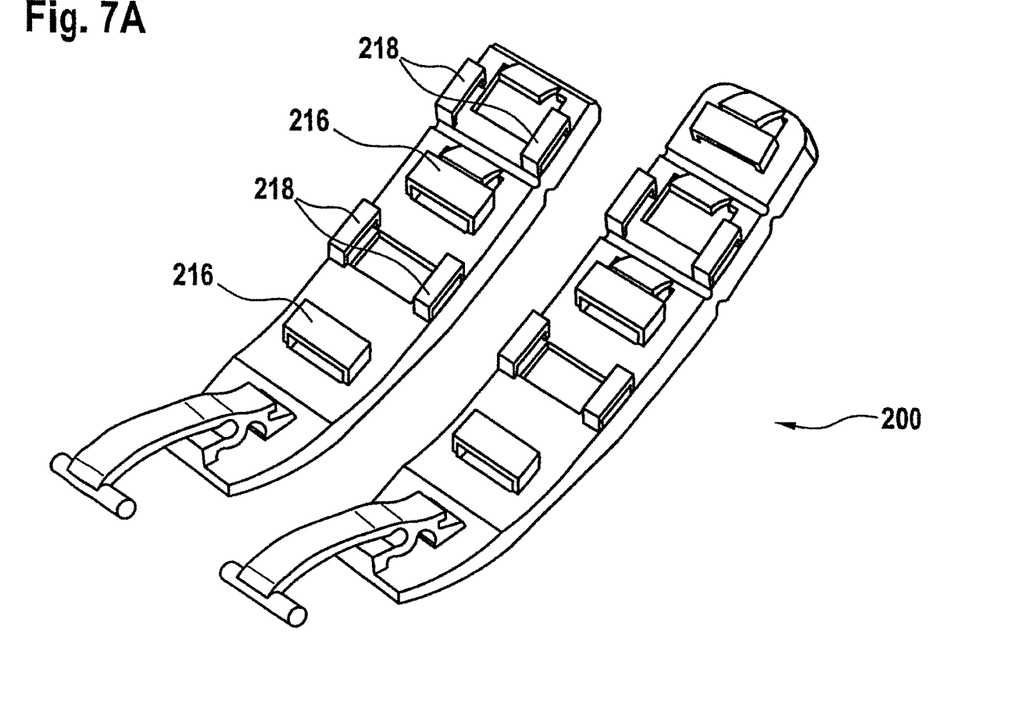
Figure 7B:
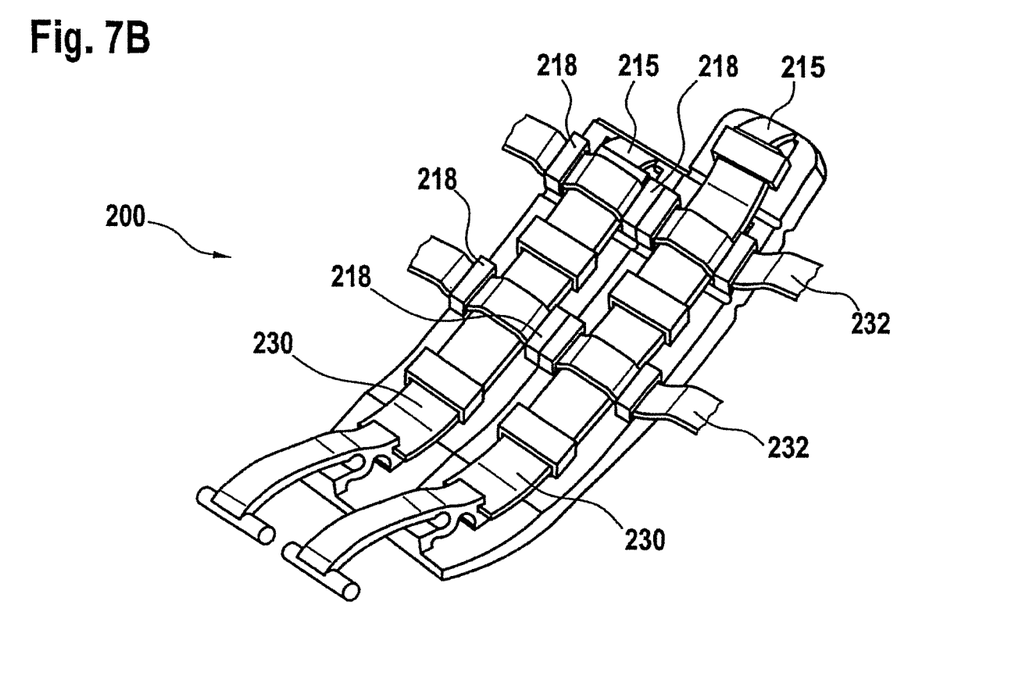

FIGS. 7A and 7B show support splints 20 with an alternative transverse coupling according to the invention. Straps 218, which are attached to the segment 212 here and can accommodate transverse coupling elements 232, in particular in the form of inelastic metal or plastic strips in order to couple at least two neighboring support splints 200 to one another. It is provided in particular that the coupling means are provided for transverse coupling of the support splints in segments.

Figure 8:
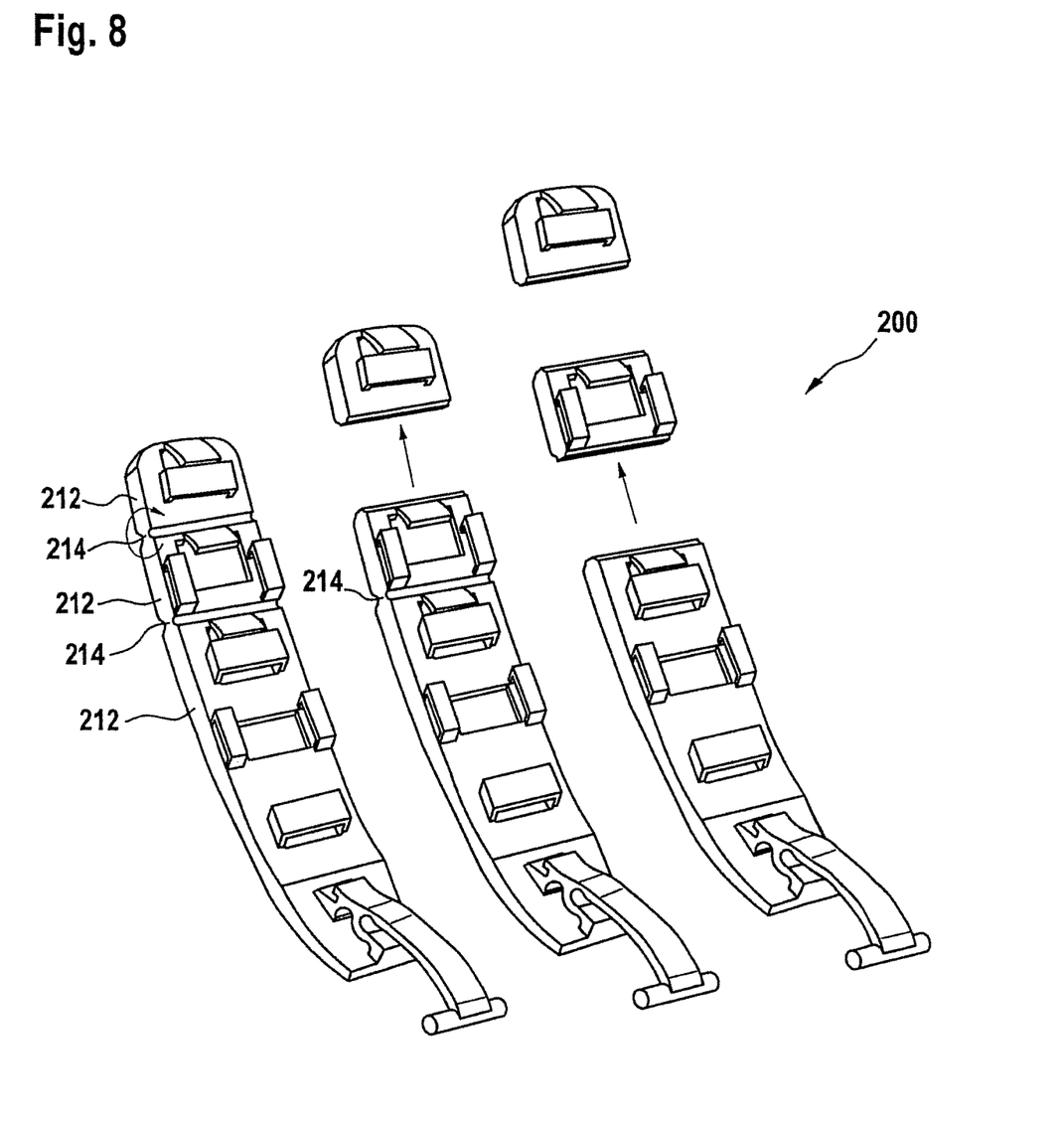

FIG. 8 illustrates schematically the function of the areas of thinner material 214 at the segment boundaries. First of all, this serves to provide an articulated connection of the segments 212 in the sense of a film joint. Secondly, it serves as an "intended breaking point," in order to make it possible to shorten the supporting splint, depending on the desired support function.

Figure 9A:
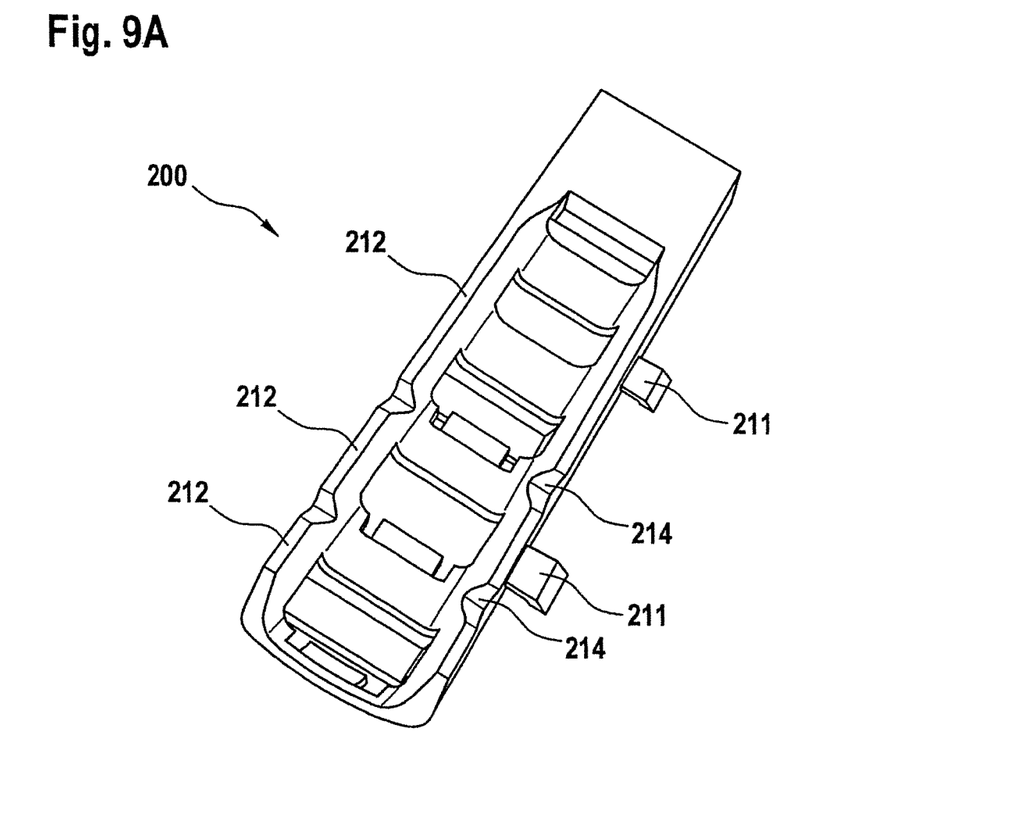
FIGS. 9A and 9B show a to view (FIG. 9A and a side view (FIG. 9B) of another support splint according to the invention.
Figure 9B:
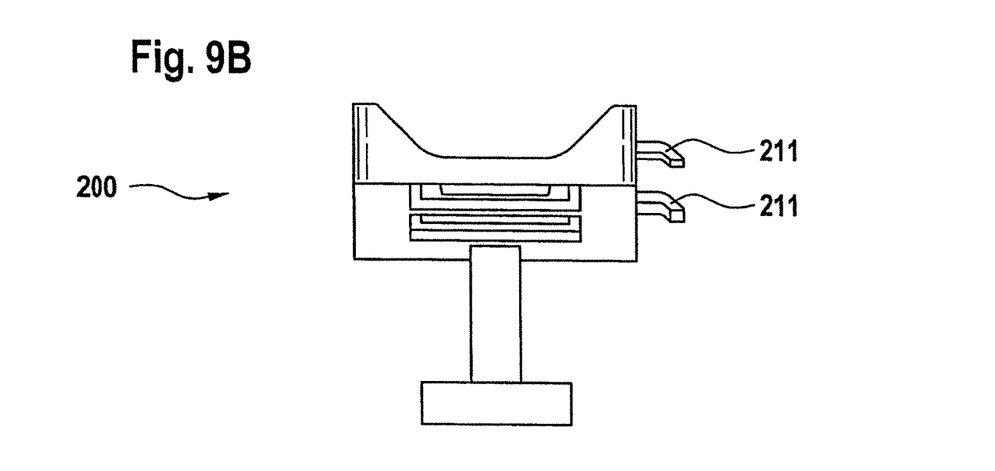

FIGS. 9A and 9B show a top view (FIG. 9A) and a side view (FIG. 9B) of the support splint to enable another structural embodiment in conjunction with the articular support according to the invention for use in a finger/hand orthotic device. On the whole, the articular splint forms a pan in which the finger to be supported is guided. The areas of thinner material 214 here is embodied in particular as notches, which suppress the reinforcing function of the edge of the pan and permit flexibility and/or severability between the segments 212.

The invention claimed is:

1. An articular support comprising:
   first and second support splints, the first support splint configured to be secured along a first digit, the second support splint configured to be secured along a second digit, both of the first and second support splints structured in a first segment and a second segment, both of the first and second segments of both of the first and second support splints including at least one transverse coupling element guide; and
   a first transverse coupling element transversely connecting the first and second support splints, the first transverse coupling element received by a first transverse coupling element guide of the first segment of the first support splint, and received a second transverse coupling element guide of the first segment of the second support splint,
   wherein the first segment of the first support splint includes a first longitudinal reinforcing element guide and the second segment of the first support splint includes a second longitudinal reinforcing element guide, and wherein the articular support further comprises a first longitudinal coupling element longitudinally connecting the first and second segments of the first support splint, the first longitudinal coupling element received by the first longitudinal reinforcing element guide and the second longitudinal reinforcing element guide.

2. The articular support of claim 1, wherein the first and second segments of at least one of the first and second support splints are connected at a hinge.

3. The articular support of claim 2, wherein the hinge is defined by a notch of thinner material.

4. The articular support of claim 1, wherein the first transverse coupling element is a rigid transverse coupling element.

5. The articular support of claim 4, wherein the rigid transverse coupling element is constructed of metal or plastic.

6. The articular support of claim 1, wherein the first transverse coupling element guides of the at least one transverse coupling element guide are arranged in pairs such that a first end of the first transverse coupling element is received by a first pair of coupling element guides and a second end of the first transverse coupling element is received by a second pair of coupling element guides.

7. The articular support of claim 1, further comprising a second transverse coupling element transversely connecting the first and second support splints, the first and second transverse coupling elements both being a rigid transverse coupling elements, the second transverse coupling element longitudinally spaced from the first transverse coupling element.

8. The articular support of claim 1, wherein the first transverse coupling element is elongated in a transverse direction extending between the first and second support splints such that the first transverse coupling element includes a length in the transverse direction and a width in a longitudinal direction, the length being greater than the width.

9. An articular support comprising:
   first and second support splints, the first support splint configured to be secured along a first digit, the second support splint configured to be secured along a second digit, both of the first and second support splints structured in a first segment and a second segment, at least one of the first and second segments of the second support splint including a transverse coupling element guide; and
   a first transverse coupling element transversely extending from at least one of the first and second segments of the first support split, the first transverse coupling element transversely connecting the first and second support splints, a free end of the first transverse coupling element received by the transverse coupling element guide of at least one of the first and second segments of the second support splint,
   wherein the transverse coupling element guide is a groove defined in a lateral side of the at least one of the first and second segments of the second support splint.

10. The articular support of claim 9, further comprising a base body including a receptacle receiving the first and second support splints.

11. The articular support of claim 10, wherein the receptacle includes a first catch for receiving the first support splint and a second catch for receiving the second support splint.

12. The articular support of claim 10, wherein the base body further includes at least one belt extending generally in a direction perpendicular to the first and second support splints.

13. The articular support of claim 9, wherein the first transverse coupling element is a rigid transverse coupling element.

14. The articular support of claim 13, wherein the rigid transverse coupling element is constructed of metal or plastic.

15. The articular support of claim 9, further comprising a second transverse coupling element transversely connecting the first and second support splints, the first and second transverse coupling elements both being a rigid transverse coupling elements, the second transverse coupling element longitudinally spaced from the first transverse coupling element.

16. The articular support of claim 9, wherein the first transverse coupling element is elongated in a transverse direction extending between the first and second support splints such that the first transverse coupling element includes a length in the transverse direction and a width in a longitudinal direction, the length being greater than the width.

* * * * *